(12) United States Patent
Inose

(10) Patent No.: US 7,220,544 B2
(45) Date of Patent: May 22, 2007

(54) METHOD FOR DETECTING TARGET NUCLEIC ACID

(75) Inventor: Ken Inose, Kyoto (JP)

(73) Assignee: Arkray, Inc., Kyoto-shi, Kyoto (JP)

( * ) Notice: Subject to any disclaimer, the term of this patent is extended or adjusted under 35 U.S.C. 154(b) by 148 days.

(21) Appl. No.: 10/511,458

(22) PCT Filed: May 8, 2003

(86) PCT No.: PCT/JP03/05773

§ 371 (c)(1),
(2), (4) Date: Oct. 13, 2004

(87) PCT Pub. No.: WO03/100095

PCT Pub. Date: Dec. 4, 2003

(65) Prior Publication Data

US 2006/0035225 A1    Feb. 16, 2006

(30) Foreign Application Priority Data

May 8, 2002   (JP)   ............................. 2003-132995

(51) Int. Cl.
*C12Q 1/68* (2006.01)
*C07H 21/04* (2006.01)
(52) U.S. Cl. .......................................... 435/6; 536/24.3
(58) Field of Classification Search ............... None
See application file for complete search history.

(56) References Cited

U.S. PATENT DOCUMENTS 6,391,593 B1 *  5/2002  Weston et al. ............. 435/91.2

FOREIGN PATENT DOCUMENTS

| EP | 0 487 218 | 5/1992 |
| EP | 0 878 554 | 11/1998 |
| EP | 0 881 302 | 12/1998 |
| EP | 1 776 215 | 1/2002 |
| JP | 05-123195 | 5/1993 |
| JP | 2002-272473 | 9/2002 |
| WO | WO 92/02638 | 2/1992 |
| WO | WO 93/05178 | 3/1993 |
| WO | WO 00/41549 | 7/2000 |
| WO | WO 03/000933 | 1/2003 |

* cited by examiner

*Primary Examiner*—Ram Shukla
*Assistant Examiner*—Amanda Shaw
(74) *Attorney, Agent, or Firm*—Knobbe, Martens, Olson & Bear, LLP

(57) ABSTRACT

A target nucleic acid having a target sequence in a sample is detected according to the steps of: (a) mixing a first probe including a nucleic acid which has a specific region having a sequence complementary to the target sequence and a nonspecific region having a sequence that is not complementary to the target sequence of the target nucleic acid; a second probe including a nucleic acid which has a first region that is complementary to at least a portion of the nonspecific region of the first probe, a loop region that does not have a sequence complementary to the first probe, and a second region that is complementary to at least a portion of the specific region of the first probe, the loop region being capable of forming a loop when it is annealed with the first probe, wherein the nucleic acid is labeled with a labeling material generating a signal by which formation of the aforementioned loop can be detected; and a sample under conditions in which the first probe and the second probe are annealed and the first probe and the target nucleic acid are annealed; and (b) detecting a signal of the labeling material.

4 Claims, 2 Drawing Sheets

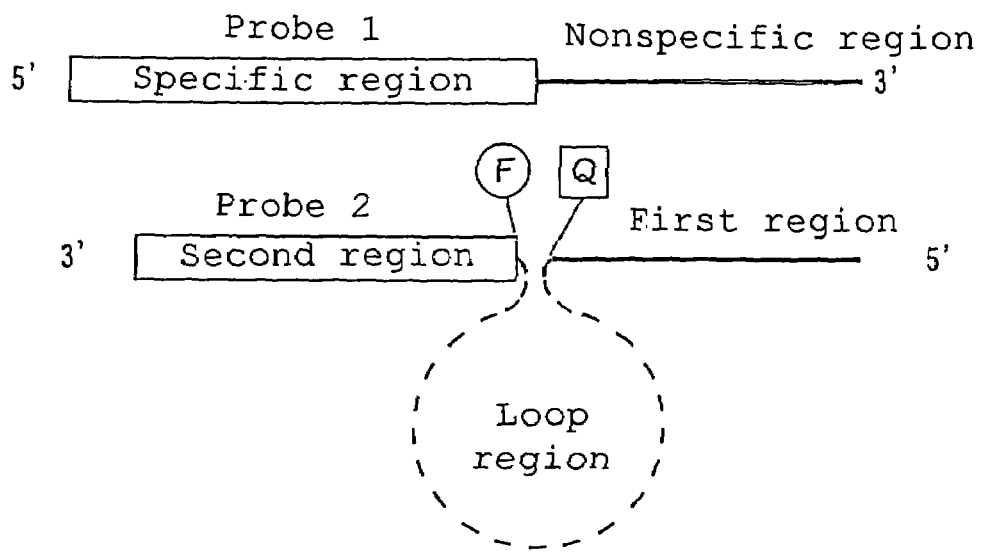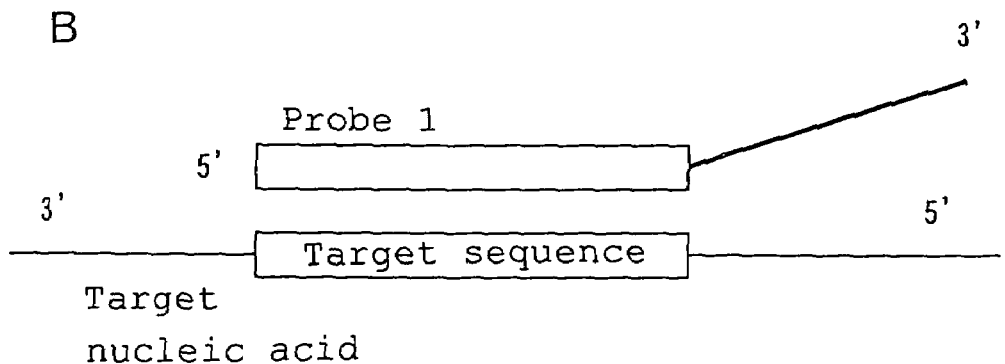
F I G. 1

METHOD FOR DETECTING TARGET NUCLEIC ACID

RELATED APPLICATIONS

This application is the U.S. National Phase under 35 U.S.C. §371 of International Application PCT/JP03/05773, filed May 8, 2003, which was published in a language other than English and which claims the priority of JP 2002-132995, filed May 8, 2002.

TECHNICAL FIELD

The present invention relates to a method and kit for detecting a target nucleic acid having a target sequence in a sample. The method and kit of the present invention permit the target nucleic acid to be detected in real time and are useful in fields of biochemistry and so forth.

BACKGROUND ART

A method for detecting a target nucleic acid having a target sequence in a sample, which has been used, includes a hybridization method in which a probe is used, a PCR method in which oligonucleotide primers are used, and other methods. Further, the PCR method is generally used in various fields including the detection and cloning of target nucleic acid, and various improved methods have been developed.

A so-called real time PCR has been known, which is a PCR method that performs amplification of a target sequence and analysis of the amplified product simultaneously. Means for analyzing the amplified products that has been known include, for example, a Taq-Man probe method (U.S. Pat. No. 5,210,015 A, JP 06-500021 A, and Holland et al., Pro. Natl. Aca. Sci. USA., 88, 7276-7280, 1991), a molecular beacon method (JP 05-123195 A, Sanjay Tyagi et al., Nature Biotechnology, vol 14, March 1996), an intercalator method (Bio/Technology, 10, 413-417, 1992, Bio/Technology, 11, 1026-1030, 1993, and JP05-237000 A), and the like.

In the Taq-Man probe method, a fluorescent material and a probe labeled with a quencher that quenches fluorescence emitted by the fluorescent material are used. When the probe is hybridized with a target nucleic acid, the quencher quenches the fluorescence while the probe is cleaved by the 5'→3' exonuclease activity of the polymerase used in PCR at the time of amplification reaction. As a result, the fluorescent material is released from the quencher to emit fluorescence. The amount of the double stranded DNA molecule can be known from this fluorescence.

Further, the molecular beacon method is a method that uses a probe including a sequence complementary to a target sequence and an arm having sequences complementary to each other at both sides thereof as well as a fluorescent material and a quencher bonded to both the ends. When the probe is annealed to the target nucleic acid, the fluorescent material emits fluorescence while when the probe is dissociated from the target nucleic acid, the probe forms an arm resulting in that the fluorescent material and the quencher become closer to each other to cause quenching.

On the other hand, the intercalator method is a method that detects a double stranded DNA using an intercalator such as ethidium bromide.

Although the methods for quantifying PCR amplified products in real time have been known as described above, they have problems; the Taq-Man probe method cannot be applied in the case of amplification methods that use polymerases having no 5'→3' exonuclease activity, the molecular beacon method is difficult to design a probe and suffers poor detection efficiency due to the intermolecular bond, and the intercalator method has no sequence specificity.

DISCLOSURE OF THE INVENTION

The present invention has been made from the aforementioned viewpoint, and it is an object of the present invention to provide a method and kit for quantifying a target nucleic acid in real time and in a simple manner without using polymerases having 5'→3' exonuclease activity.

The inventors of the present invention have made extensive studies in order to achieve the aforementioned object and as a result they have found that use of two types of probes differing in length enables quantification of a target nucleic acid in a simple manner, thereby accomplishing the present invention.

That is, the present invention relates to:

(1) A method for detecting a target nucleic acid having a target sequence in a sample, comprising the steps of:

(a) mixing a first probe including a nucleic acid which has a specific region having a sequence complementary to the target sequence and a nonspecific region having a sequence that is not complementary to the target sequence of the target nucleic acid; a second probe including a nucleic acid which has a first region that is complementary to at least a portion of the nonspecific region of the first probe, a loop region that does not have a sequence complementary to the first probe, and a second region that is complementary to at least a portion of the specific region of the first probe, the loop region being capable of forming a loop when it is annealed with the first probe, wherein the nucleic acid is labeled with a labeling material generating a signal by which formation of the aforementioned loop can be detected; and a sample under conditions in which the first probe and the second probe are annealed and the first probe and the target nucleic acid are annealed; and (b) detecting a signal of the labeling material.

(2) A method according to item (1), wherein the second region of the second probe is shorter than the specific region of the first probe.

(3) A method according to item (1) or (2), wherein the labeling material comprises a fluorescent material and a quencher that quenches the fluorescence of the fluorescent material when the quencher is near the fluorescent material, arranged so as to sandwich the loop region, with the fluorescence of the fluorescent material being quenched by the quencher when the first probe and the second probe are annealed to form the loop and not quenched when the first probe and the second probe are not annealed as compared when the probes are annealed.

(4) A method according to any one of items (1) to (3), wherein the detection of the signal is performed quantitatively, thereby quantifying the target nucleic acid.

(5) A kit for detecting a target nucleic acid having a target sequence in a sample, comprising a first probe including a nucleic acid which has a specific region having a sequence complementary to the target sequence and a nonspecific region having a sequence that is not complementary to the target sequence of the target nucleic acid; a second probe including a nucleic acid which has a first region that is complementary to at least a portion of the nonspecific region of the first probe, a loop region that does not have a sequence complementary to the first probe, and a second region that is complementary to at least a portion of the specific region of the first probe, the loop region being capable of forming a loop when it is annealed with the first probe, wherein the nucleic acid is labeled with a labeling material generating a signal by which formation of the aforementioned loop can be detected.

BRIEF DESCRIPTION OF THE DRAWINGS

FIG. 1 is schematic diagrams illustrating the concept of the present invention, with F indicating a fluorescent material and Q indicating a quencher.

BEST MODE FOR CARRYING OUT THE INVENTION

Figure 2:
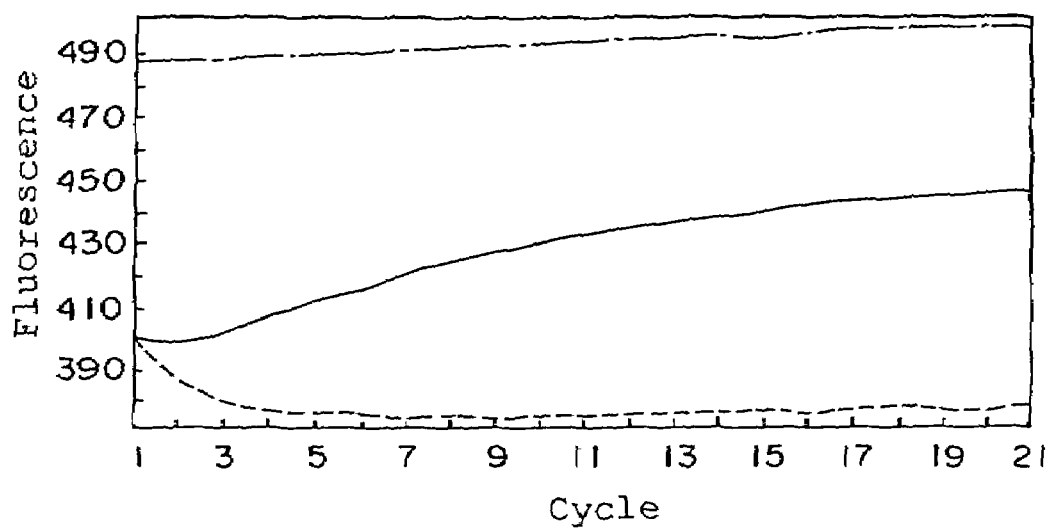
FIG. 2 is a graph showing the time-course changes of the intensities of fluorescence of the reaction mixtures (not subjected to heat treatment), where solid line: Probe 1+Probe 2+target oligonucleotide
dotted line: Probe 1+Probe 2
alternate longer and shorter dashed lines: Probe 2.

Hereinafter, the present invention will be described in detail.

The method of the present invention is a method for detecting a target nucleic acid having a target sequence in a sample. The target nucleic acid is not particularly limited so far as it has the target sequence; it may be either a DNA or an RNA, and it may be either single stranded or double stranded. The present invention is advantageously applied to detection of particularly a double stranded DNA. In a preferable mode of the present invention, the target nucleic acid is detected quantitatively. Note that quantitative detection includes measurement of an absolute amount of a nucleic acid and measurement of a nucleic acid relatively to a certain amount.

The target sequence is usually a sequence specific to the target nucleic acid and is not particularly limited in sequence and length so far as it can form a specific hybrid with a probe having a sequence complementary to that sequence. The length of the target sequence is preferably 6 bases or more, more preferably 15 bases or more.

Samples that contain the target nucleic acid are not particularly limited and include nucleic acids or nucleic acid mixtures extracted from cells or tissues, and PCR nucleic acid amplification reaction mixtures using such nucleic acids or nucleic acid mixtures as templates.

In the present invention, two types of probes are used in detecting the target nucleic acid (see FIG. 1). A first probe (hereinafter, also referred to as "Probe 1") includes a nucleic acid which has a specific region having a sequence complementary to the target sequence and a nonspecific region having a sequence that is not complementary to the target sequence of the target nucleic acid (FIG. 1A). Due to such a structure, when Probe 1 is hybridized with the target nucleic acid, the nonspecific region remains as a single strand and forms a flap (FIG. 1B). The length of the nonspecific region is preferably 10 bases or more, more preferably 10 to 30 bases.

A second probe (hereinafter, also referred to as "Probe 2") includes a nucleic acid which has a first region that is complementary to at least a portion of the aforementioned nonspecific region of the Probe 1, a loop region that does not have a sequence complementary to Probe 1, and a second region that is complementary to at least a portion of the specific region of Probe 1, the loop region being capable of forming a loop when it is annealed with Probe 1, and the nucleic acid is labeled with a labeling material generating a signal by which formation of the aforementioned loop can be detected (FIG. 1A).

Note that FIG. 1 shows examples of Probe 1 that has the specific region on the 5' side and the nonspecific region on the 3' side and of Probe 2 that has the first region, the loop region, and the second region in order from the 5' side. In the present invention, Probe 1 may have the specific region on the 3' side and the nonspecific region on the 5' side and Probe 2 may have the first region, the loop region, and the second region in order from the 3' side.

The first region has a sequence that is complementary to at least a portion of the nonspecific region of Probe 1 and preferably has a sequence that is complementary to the whole nonspecific region. On the other hand, the second region has a sequence that is complementary to at least a portion of the specific region of Probe 1 and preferably is shorter than the specific region. By making the second region shorter than the specific region, Probe 1 can be annealed with the target nucleic acid preferentially than Probe 2. The length of the second region is preferably 6 bases or more, more preferably 6 to 20 bases. Alternatively, it is desirable that the second region is made shorter by preferably one base or more, more preferably 4 bases or more than the specific region.

The loop region is a region that does not have a sequence complementary to Probe 1 and preferably it does not have a sequence complementary to the target nucleic acid. The loop region forms a protruded portion in the form of a loop when Probe 2 is bonded to Probe 1 but when Probe 2 and Probe 1 are dissociated from each other, the loop structure is eliminated (FIG. 1C). Probe 2 is labeled with a labeling material generating a signal by which formation of a loop can be detected. The labeling material specifically includes, for example, an energy donor and an energy receptor arranged so as to sandwich the loop region. The energy donor and energy receptor include, for example, a fluorescent material and a quencher that quenches the fluorescence generated by the fluorescent material. The quencher quenches fluorescence when it is near the fluorescent material but it will no longer quench fluorescence when the distance between the fluorescent material and the quencher is equal to or greater than a certain distance. With such a fluorescent material and quencher, the fluorescence of the fluorescent material is quenched by the quencher when Probe 1 and Probe 2 are annealed to form a loop while the fluorescence is not quenched when Probe 1 and Probe 2 are not annealed. Therefore, by measuring the fluorescence from the fluorescent material, formation of a loop, that is the state of hybridization of Probe 1 and Probe 2 can be detected. Examples of the fluorescent material include fluorescein dyes such as fluorescein and fluorescein isothiocyanate (FITC) and examples of the quencher include rhodamine dyes such as tetramethyl rhodamine isothiocyanate (TRITC) and Sulfo Rhodamine 101 chlorosulfonate derivative (trade name: Texas Red). Among these, a preferable combination is FITC and Texas Red. These labeling materials can be introduced into any desired portion of the sequence by performing chemical synthesis of Probe 2 using oligonucleotides having bonded thereto these labeling materials. Any of the fluorescent material and quencher may be on the 5' side.

The sequence and length of the loop region are not particularly limited so far as a loop structure is formed when Probe 1 and Probe 2 are annealed and signals from the labeling material differ between the case where the loop structure is formed and the case where it is eliminated. Note that the loop region is preferably designed such that the loop region forms neither a partial double strand with the first region and second region of Probe 2 nor a partial double strain within the loop region. The length of the loop region is preferably 10 bases or more and more preferably 20 bases or more. It is desirable that the labeling material is bonded to a portion usually within 3 bases form the both terminal bases in the loop region, preferably to the terminal bases.

The aforementioned Probe 1, Probe 2, and a sample are mixed in the conditions under which Probe 1 and Probe 2 are annealed and Probe 1 and the target nucleic acid are annealed. However, from the aforementioned structures of the probes, Probe 1 is annealed with the target nucleic acid preferentially than Probe 2. The order of mixing in not particularly questioned; for example, Probe 1 and Probe 2 are mixed and then the sample is added. Further, a premixture of Probe 1 and Probe 2 may be prepared in advance. Furthermore, it is preferable that a reaction mixture that does not contain Probe 1 and/or a sample is used as a control.

Probe 1 and Probe 2 are mixed in a molar ratio of preferably 1:1. The final concentration of each of Probe 1 and Probe 2 in the reaction mixture is preferably 0.1 µM or more.

After Probe 1, Probe 2, and the sample are mixed, either the mixture as it is may be exposed to the conditions in which Probe 1 and Probe 2 are annealed and Probe 1 and the target nucleic acid are annealed or the mixture may be subjected to heat denaturation treatment and then exposed to the aforementioned conditions.

Figure 3:
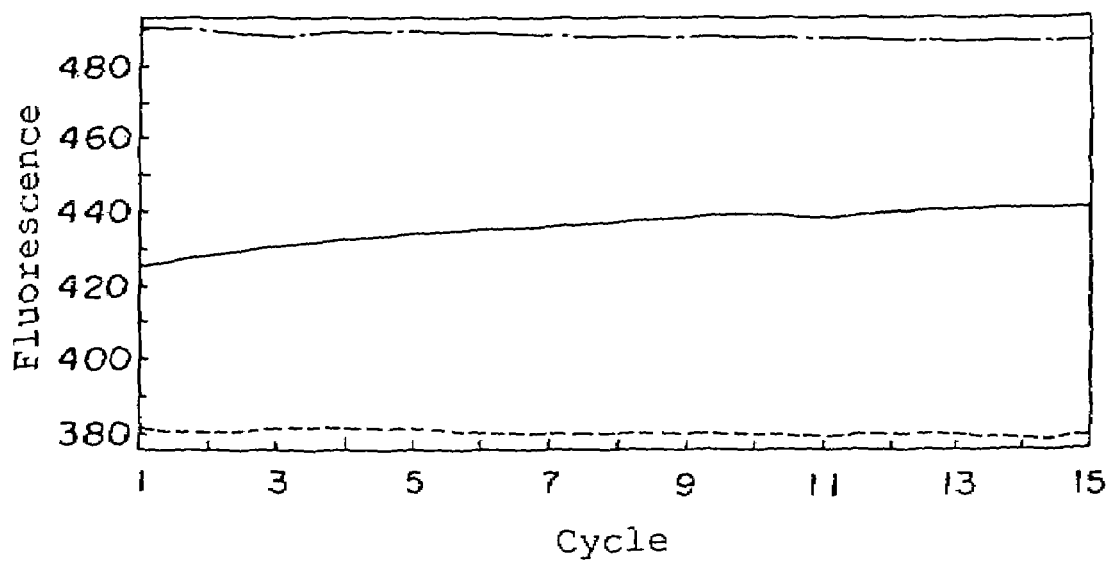
FIG. 3 is a graph showing the time-course changes of intensities of fluorescence of the reaction mixtures (subjected to heat treatment).

After leaving the aforementioned reaction mixture to stand a given time, preferably after it has reached an equilibrium state, the signal of the labeling material is detected. More preferably, the detection of the signal is performed with time. The aforementioned conditions include, for example, a temperature that is lower by 3 to 10° C. than the (Tm) s of Probe 1 and Probe 2. Optimal conditions can be readily determined by performing detection of signals with time with varying temperature in several stages to select those that give the clearest difference from the control. In the case where FITC is used as a fluorescent material and Texas is used Red as a quencher, the detection of signals is performed by measuring intensity of fluorescence at a fluorescent wavelength of 515 nm attributable to FITC. The measurement of the intensity of fluorescence is performed using a commercially available apparatus. The results of the measurements are shown in FIGS. 2 and 3. Those results will be described in detail in the example below.

By quantitatively detecting the signals of the labeling material, the amount of the target nucleic acid can be quantified.

The kit of the present invention is a kit that is used in order to detect the aforementioned target nucleic acid and includes Probe 1 and Probe 2. Each probe may be either a solution or a freeze-dried preparation. Further, each probe may be either charged in a separate container or in the same container as a mixture. The kit of the present invention may further contain a buffer for dissolving or diluting each probe or a sample.

The method and kit of the present invention can be advantageously used in quantifying the amplified product in the nucleic acid amplification reaction mixture in a real time.

The kit of the present invention may contain an oligonucleotide primer for amplifying such a target nucleic acid by a nucleic acid amplification method. The primer is charged in a separate container from that in which each probe is contained.

EXAMPLE

Hereinafter, the present invention will be described in more detail by examples.

Probe 1 (SEQ ID NO: 1), Probe 2 (SEQ ID NO: 2), and a target oligonucleotide (SEQ ID NO: 3) were synthesized. The synthesis of each oligonucleotide was requested to Japan Bio Service Co., Ltd. The nucleotide (T) of the base 21 of Probe 2 was labeled with FITC and the nucleotide (T) of base 52 was labeled with Texas Red. Note that the target oligonucleotide is a partial sequence of human amylin gene.

The bases 1 to 28 of Probe 1 are complementary to the bases 6 to 33 of the target oligonucleotide. The bases 11 to 33 and bases 35 to 55 of Probe 1 are complementary to the bases 52 to 74 and bases 1 to 21 of Probe 2, respectively. Note that the bases 57 to 74 of SEQ ID NO: 2 is homologous to the bases 6 to 23 of SEQ ID NO: 3.

Each oligonucleotide was dissolved in TE buffer to 5 µM. In a 1.5-ml tube were added 2.2 µl of 10×Ex Taq buffer (Takara Shuzo Co., Ltd., Lot. A6501-1), 19.8 µl of sterilized distilled water, and 1 µl of a Probe 2 solution (5 µM), which were mixed well and 23 µl of the mixture was dispensed to each 25-µl tube for a reaction machine (Cepheid Co., Smart Cycler). In each tube, 1 µl of the Probe 1 solution (5 µM) or TE buffer was added and further 1 µl of the target oligonucleotide solution (5 µM) or TE buffer to obtain a reaction mixture. This operation was performed at room temperature.

The aforementioned reaction mixture or the aforementioned reaction mixture subjected to heat treatment at 94° C. for 3 minutes was set in the Smart Cycler, which was adjusted to 47° C. and fluorescence at a wavelength of 505 to 537 nm was measured. The results on the reaction mixture that was not subjected to the heat treatment are shown in FIG. 1 and the results on the reaction mixture subjected to the heat treatment are shown in FIG. 2.

With Probe 2 only, fluorescence was observed but in the case where Probe 1 was added, the fluorescence was quenched considerably. In the case where the target oligonucleotide in addition to Probe 1 was added to Probe 2, fluorescence with an intermediate intensity between both the cases was observed. The results were the same regardless of presence or absence of the heat treatment.

As described above, higher intensity of fluorescence observed in the case where the target sequence was present than the case where no target sequence was present confirmed that Probe 1 preferentially bonds to the target sequence than Probe 2 and a portion of Probe 2 was free.

INDUSTRIAL APPLICABILITY

By the present invention, a target nucleic acid can be quantified in a real time and in a simple manner. The method of the present invention does not require a polymerase having a 5'→3' exonuclease activity, so that it can be applied to various reaction systems.

What is claimed is:

1. A method for detecting a target nucleic acid having a target sequence in a sample, comprising the steps of:
   (a) obtaining a first probe comprising a nucleic acid which has a specific region having a sequence complementary to the target sequence and a nonspecific region having a sequence that is not complementary to the target sequence of the target nucleic acid; and a second probe comprising a nucleic acid which has a first region that is complementary to at least a portion of the nonspecific region of the first probe, a loop region that does not have a sequence complementary to the first probe, and a second region that is complementary to at least a portion of the specific region of the first probe, wherein the nucleic acid of the second probe is labeled with a labeling material generating a signal by which formation of a loop can be detected;
   (b) mixing the first probe and the second probe, thereby forming a mixture wherein the loop in the loop region of the second probe is formed when the second probe is annealed with first probe, thereby quenching the signal from the labeling material in the absence of a target nucleic acid;
   (c) adding the sample to the mixture of step (b), whereby the target nucleic acid in the sample anneals with the first probe, thereby releasing the second probe; and
   (d) detecting an increase in the signal of the labeling material in the presence of the target nucleic acid compared to the signal obtained in step (b), thereby detecting the target nucleic acid, wherein the signal is quenched when the first probe and the second probe are annealed and not quenched when the first probe and the second probe are not annealed.

2. The method according to claim 1, wherein the second region of the second probe is shorter than the specific region of the first probe.

3. The method according to claim 1, wherein the labeling material comprises a fluorescent material and a quencher that quenches a fluorescence of the fluorescent material when the quencher is near the fluorescent material, arranged so as to sandwich the loop region, with the fluorescence of the fluorescent material being quenched by the quencher when the first probe and the second probe are annealed to form the loop and not quenched when the first probe and the second probe are not annealed.

4. The method according to claim 1, wherein the detection of the increase in the signal is performed quantitatively, thereby quantifying the target nucleic acid.

* * * * *

UNITED STATES PATENT AND TRADEMARK OFFICE
CERTIFICATE OF CORRECTION

PATENT NO. : 7,220,544 B2  Page 1 of 1
APPLICATION NO. : 10/511458
DATED : May 22, 2007
INVENTOR(S) : Ken Inose It is certified that error appears in the above-identified patent and that said Letters Patent is hereby corrected as shown below:

Title Page, (30) Foreign Application Priority Data, "2003-132995" should be changed to --2002-132995--

Signed and Sealed this

Sixth Day of November, 2007

JON W. DUDAS
*Director of the United States Patent and Trademark Office*

UNITED STATES PATENT AND TRADEMARK OFFICE
CERTIFICATE OF CORRECTION

PATENT NO. : 7,220,544 B2
APPLICATION NO. : 10/511458
DATED : May 22, 2007
INVENTOR(S) : Ken Inose Page 1 of 1

It is certified that error appears in the above-identified patent and that said Letters Patent is hereby corrected as shown below:

Title Page, Column 2, Item [56] Foreign Patent Documents, 4th Entry, "EP 1 776 215"

should be changed to --EP 1 176 215--

Column 5, Line 46, "Texas is used Red as a quencher," should be changed to --Texas Red is used as a quencher--

Column 7, Line 60, Claim 1 "annealed with first probe," should be changed to

--annealed with the first probe--

Signed and Sealed this

Twenty Second Day of April, 2008

JON W. DUDAS
*Director of the United States Patent and Trademark Office*

SEQUENCE LISTING

<160> NUMBER OF SEQ ID NOS: 3

<210> SEQ ID NO 1
<211> LENGTH: 56
<212> TYPE: DNA
<213> ORGANISM: Artificial Sequence
<220> FEATURE:
<223> OTHER INFORMATION: Description of Artificial Sequence: probe 1

<400> SEQUENCE: 1
aaagttgttg ctggaatgaa ctaaaaaatg gcaatattca catgtacagg actcag        56

<210> SEQ ID NO 2
<211> LENGTH: 75
<212> TYPE: DNA
<213> ORGANISM: Artificial Sequence
<220> FEATURE:
<223> OTHER INFORMATION: Description of Artificial Sequence: probe 2

<400> SEQUENCE: 2
ctgagtccag tacaactgaa taaaaaaaaa aaaaaaaaa aaaaaaaaaa attgccattt        60
tttagttcat tccag        75

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: target
      oligonucleotide

<400> SEQUENCE: 3
ggcaaatttt ttagttcatt ccagcaacaa ctttggtgcc attctctcat        50